US00PP17537P3

(12) United States Plant Patent
Gagnon et al.

(10) Patent No.: US PP17,537 P3
(45) Date of Patent: Mar. 27, 2007

(54) SYCAMORE MAPLE TREE NAMED 'TUNPETTI'

(50) Latin Name: *Acer pseudoplatanus*
Varietal Denomination: Tunpetti

(75) Inventors: Paul Gagnon, Arva (CA); Barbara Ann Gagnon, Arva (CA)

(73) Assignee: PBA Tundra Supply Ltd, Arva (CA)

( * ) Notice: Subject to any disclaimer, the term of this patent is extended or adjusted under 35 U.S.C. 154(b) by 0 days.

(21) Appl. No.: 11/196,442

(22) Filed: Aug. 4, 2005

(65) Prior Publication Data

US 2006/0031974 P1 Feb. 9, 2006

(51) Int. Cl.
*A01H 5/00* (2006.01)

(52) U.S. Cl. ..... Plt./224

(58) Field of Classification Search ..... Plt./224
See application file for complete search history.

*Primary Examiner*—Kent Bell
*Assistant Examiner*—June Hwu
(74) *Attorney, Agent, or Firm*—Standley Law Group LLP

(57) ABSTRACT

A sycamore maple tree named 'Tunpetti' having unique foliage color. In summer, the upper leaf surface is dark green, and the underside is greyed burgundy in color with vibrant red petioles. The foliage changes to a superb bright yellow upper and warm pink lower surface color during autumn. The bark of 'Tunpetti' is uniform and smooth with only a slight scaliness and limited vertical fissuring. In addition, 'Tunpetti' has been observed to be exceptionally resistant to "tar spot", a leaf disease common amongst *Aceraceae*.

9 Drawing Sheets

Latin name: *Acer pseudoplatanus.*
Variety denomination: 'Tunpetti'.

FIELD OF THE INVENTION

The present invention relates to a new and distinct variety of sycamore maple tree named 'Tunpetti'. Although the exact origin and parentage of this new sycamore maple is unknown, it is believed to be a variety of *Acer pseudoplatanus.* The tree has particular utility in landscaping as an aesthetically pleasing shade tree.

SUMMARY OF THE INVENTION

The new variety has unique foliage colour. In summer, the upper leaf surface is dark green, and the underside is greyed burgundy in colour with vibrant red petioles. The foliage changes to a superb bright yellow upper and warm pink lower surface colour during autumn. The bark of 'Tunpetti' is uniform and smooth with only a slight scaliness and limited vertical fissuring. In addition, 'Tunpetti' has been observed to be exceptionally resistant to "tar spot", a leaf disease common amongst *Aceraceae.*

The original sycamore maple tree of the present invention was discovered in a cultivated, landscaped area in Hubbards, Nova Scotia, Canada (44° 38' N., 64° 3.2' W.) on Aug. 12, 2002 among a group of three trees. The area is situated approximately 300 feet from the Atlantic Ocean in an organic soil with a high percentage of silt. The initial observation of distinctive foliage coloration and bark character led to the removal and transplanting of one of the trees, with an estimated age of about three years, for further study. Asexual reproduction of the tree was performed under the inventors' direction by Anthony Zimmerman at his nursery in Strathroy, Ontario, Canada by both bud and rootstock grafting onto *Acer pseudoplatanus* stock. Successive asexual propagations and observations of the resulting progeny have established that the initially observed foliage coloration and bark character are stable and reproducible cultivar traits. This foliage coloration and bark character are believed to be new and unique in *Acer pseudoplatanus,* making this variety new and patentably distinct from other trees of the species.

The new sycamore maple variety 'Tunpetti' is readily distinguishable in foliage coloration from prior art *Acer pseudoplatanus* varieties, which typically have a similar leaf colour on the upper and lower surfaces. By way of example, the *A. pseudoplatanus* variety 'Spaethii' has the following summer foliage coloration:

Leaf upper surface: R.H.S 137A
Leaf lower surface: R.H.S. N186A
Petiole upper surface: R.H.S. 176A
Petiole lower surface: R.H.S.144B The vibrant and dramatic fall coloration of 'Tunpetti' is particularly aesthetically pleasing as compared with the prior art variety 'Spaethii'.

Further features of the maple tree 'Tunpetti' will be described or will become apparent in the course of the following description.

BRIEF DESCRIPTION OF THE PHOTOGRAPHS

The accompanying colour photographs taken using conventional colour film photography and digital photography show as truly as possible the colour, shape and texture of the maple tree 'Tunpetti' and parts thereof. The photographs are of trees and parts thereof grown in London, Ontario, Canada.

FIG. 1*a* is a photograph showing the upper leaf surface during autumn;

FIG. 1*b* is a photograph showing the lower leaf surface during autumn;

FIG. 2*a* is a photograph showing the upper leaf surface during summer;

FIG. 2*b* is a photograph showing the lower leaf surface during summer;

Figure 1A:
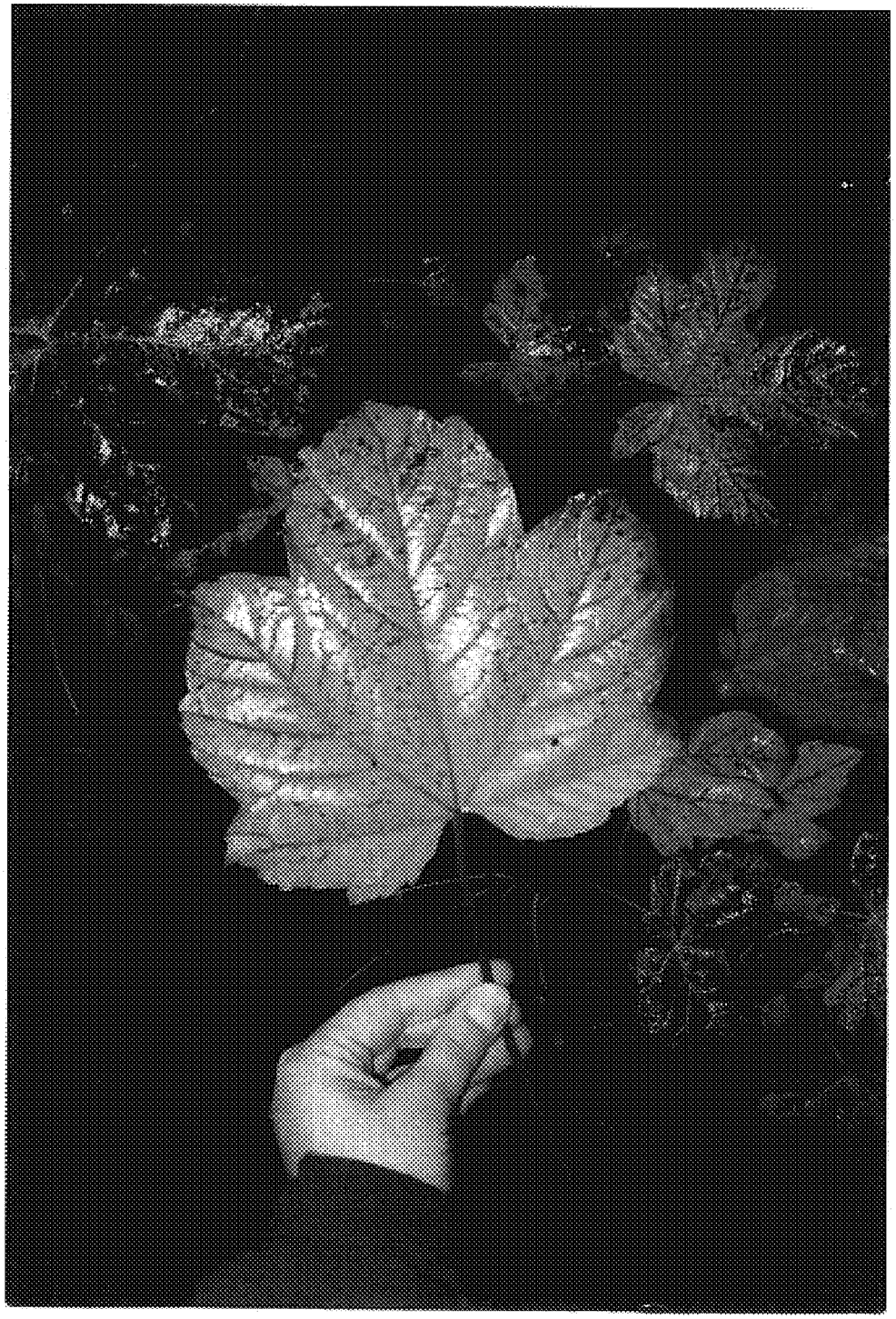
Figure 1B:
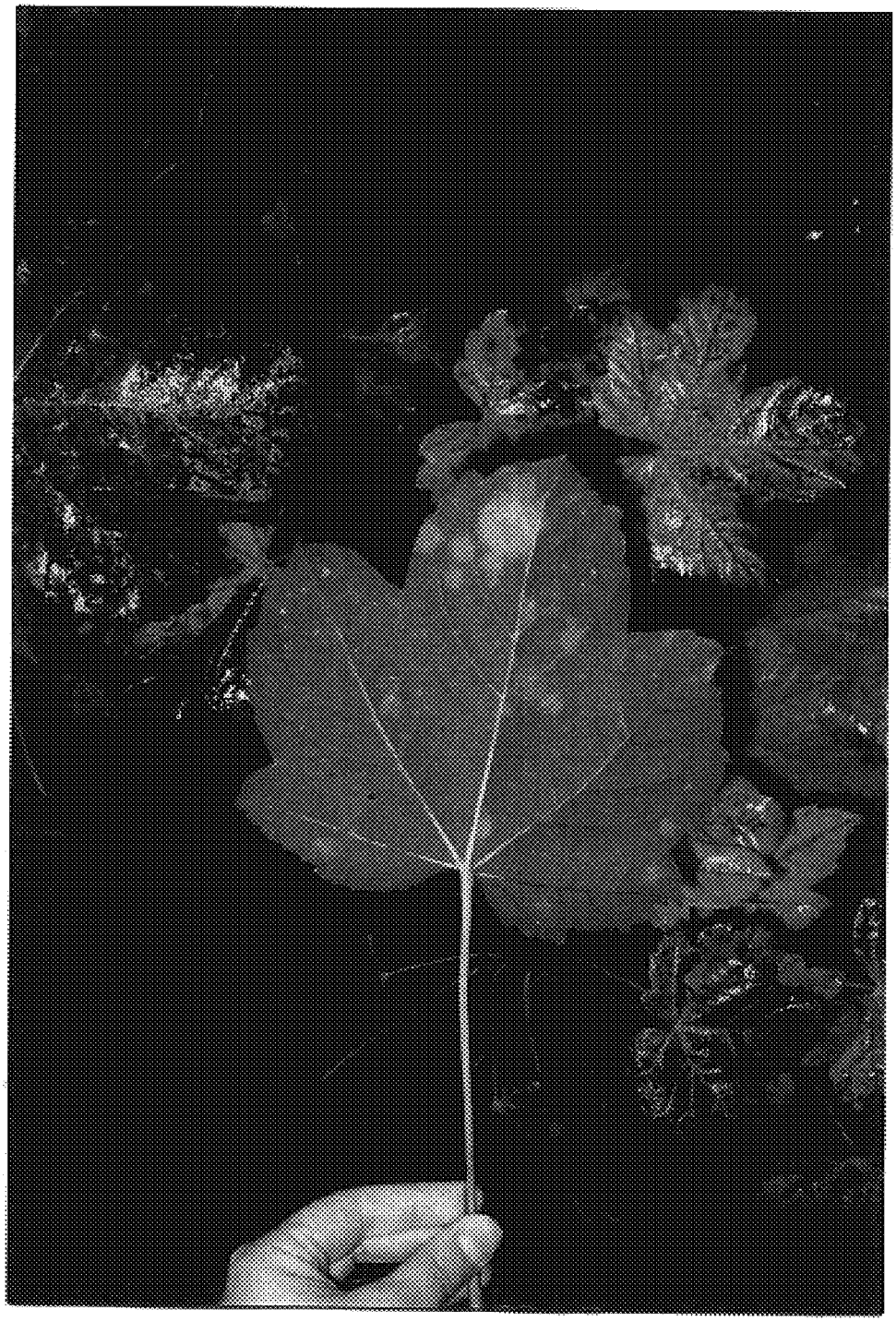
Figure 2A:
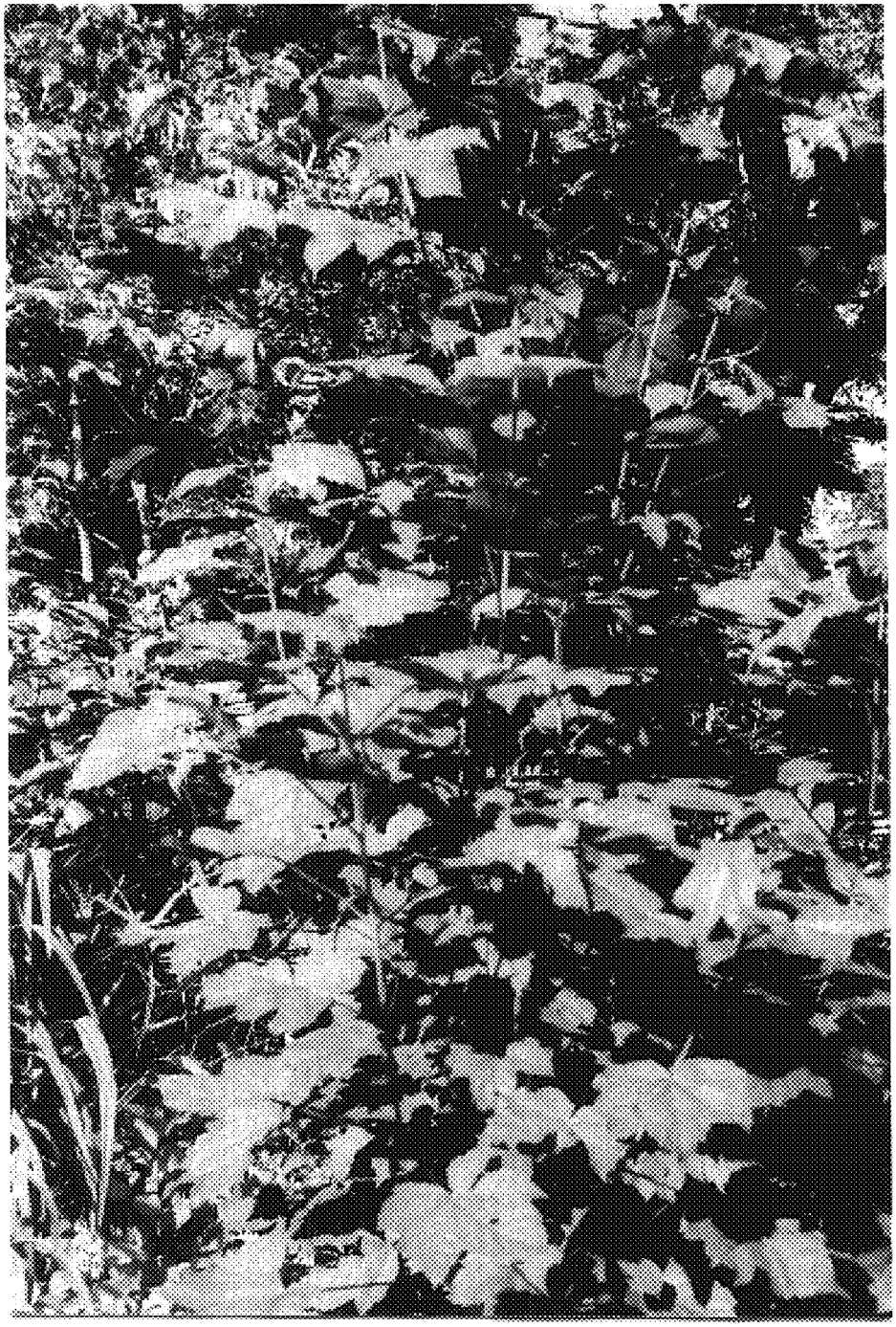
Figure 2B:
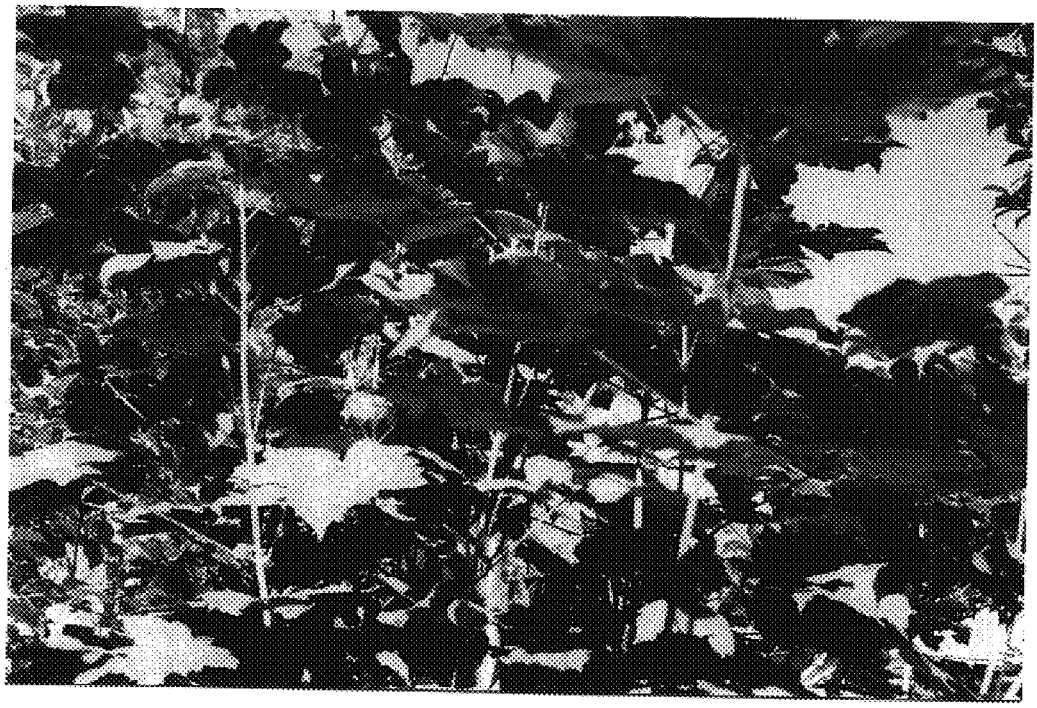
Figure 3:
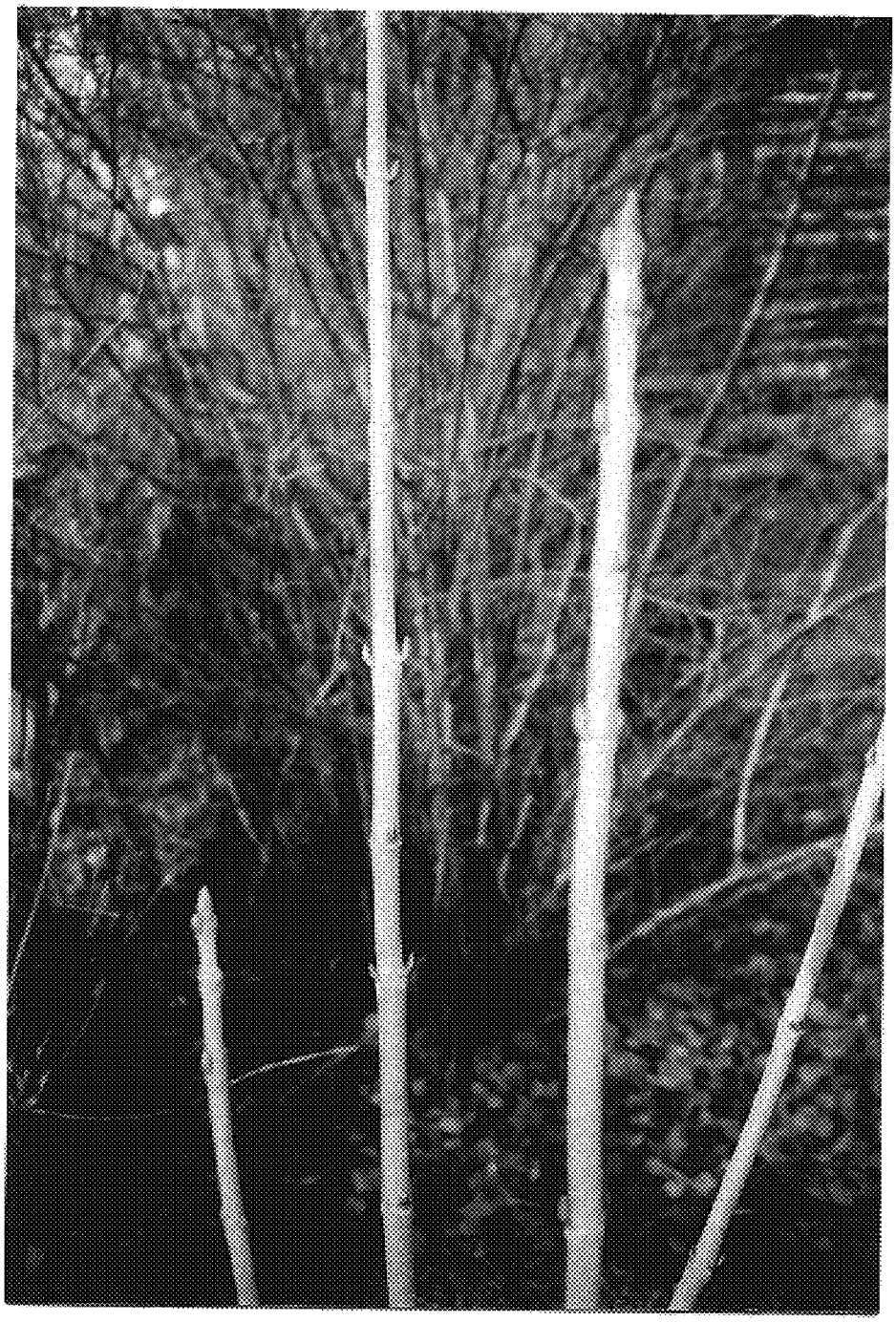
FIG. 3 is a photograph showing the tree bark and buds in spring.
Figure 4:
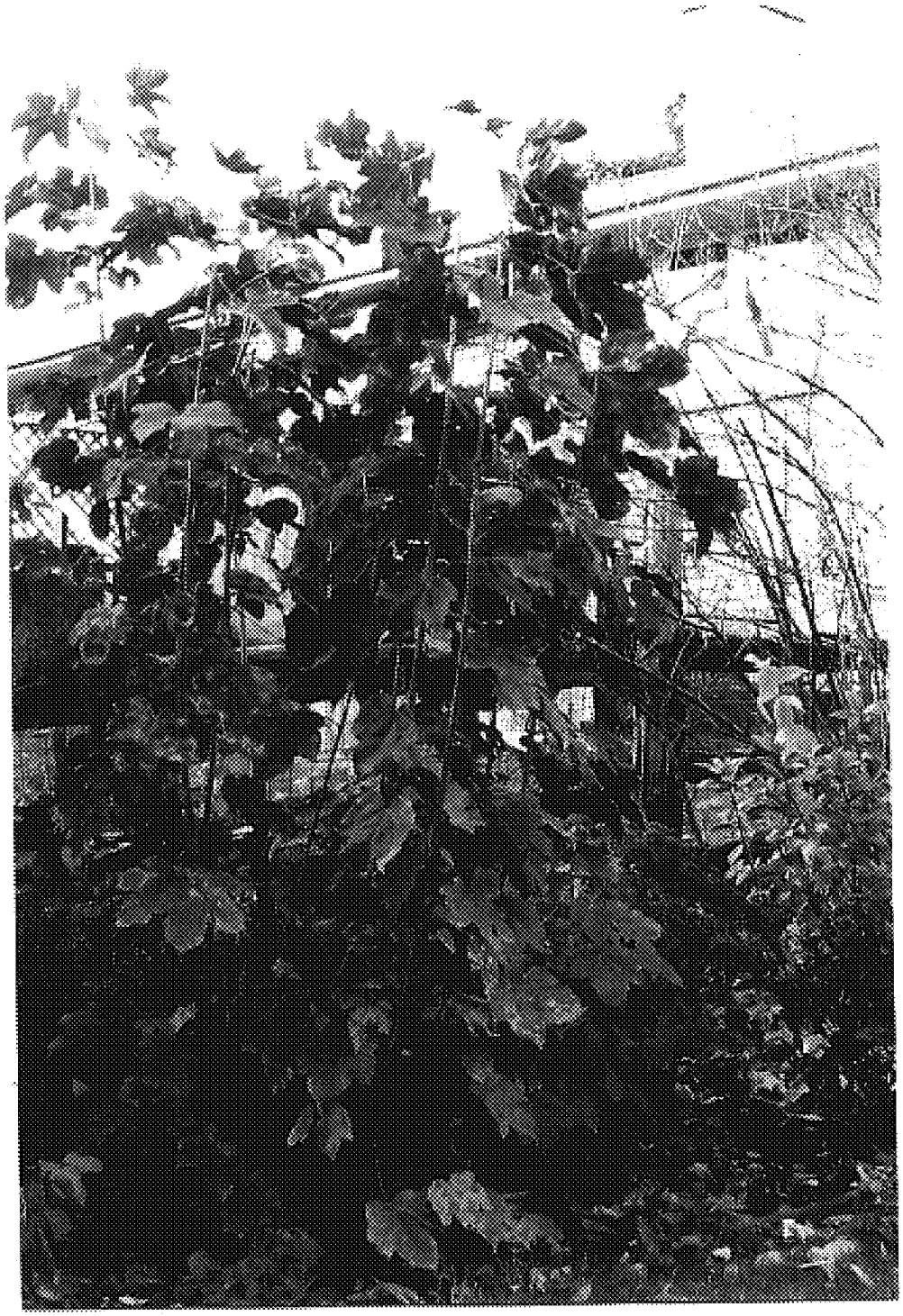
FIG. 4 is a photograph showing the tree in late summer/early autumn.
Figure 5A:
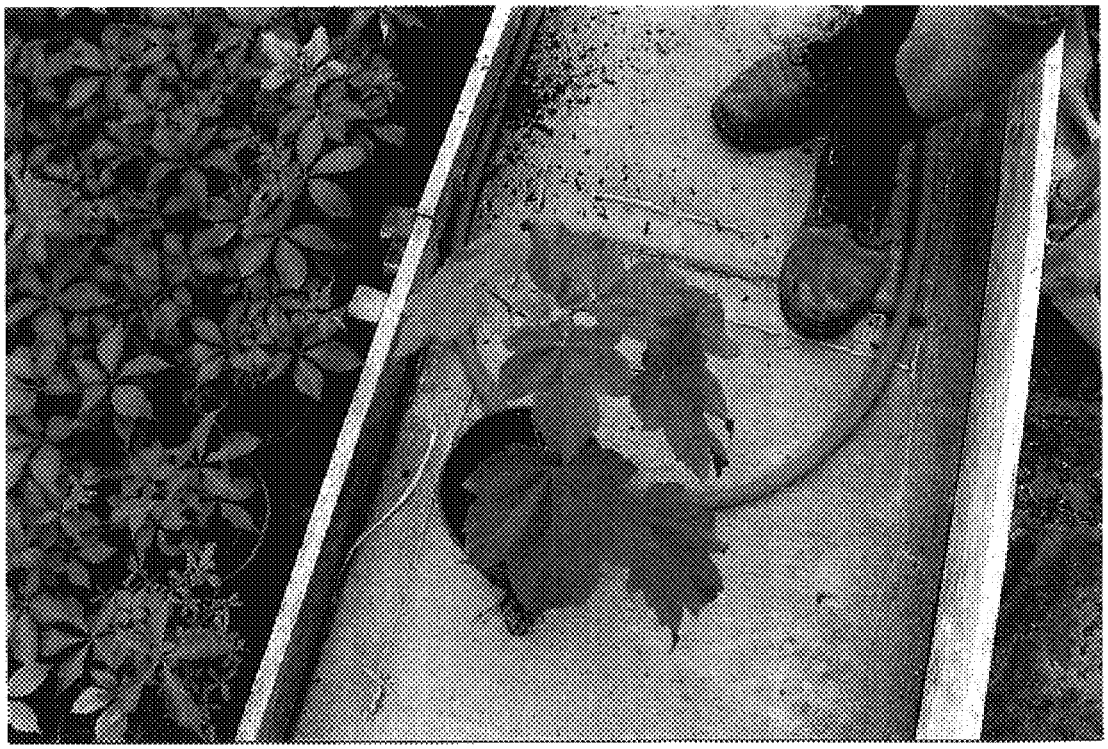
Figure 5B:
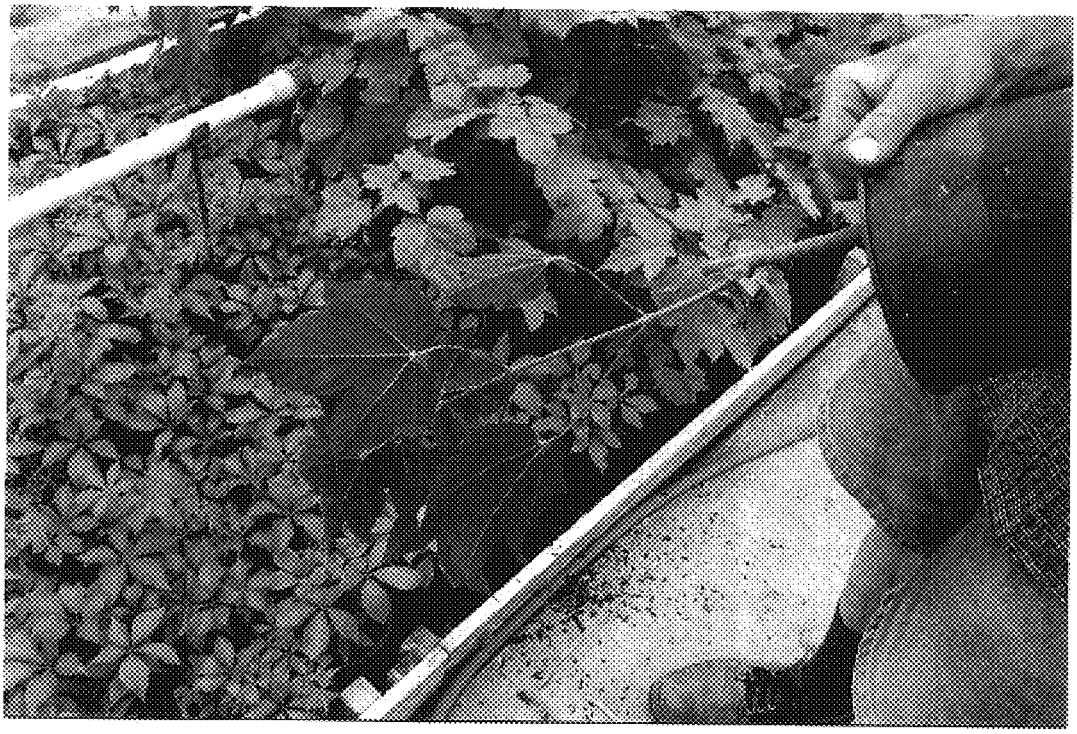
Figure 6:
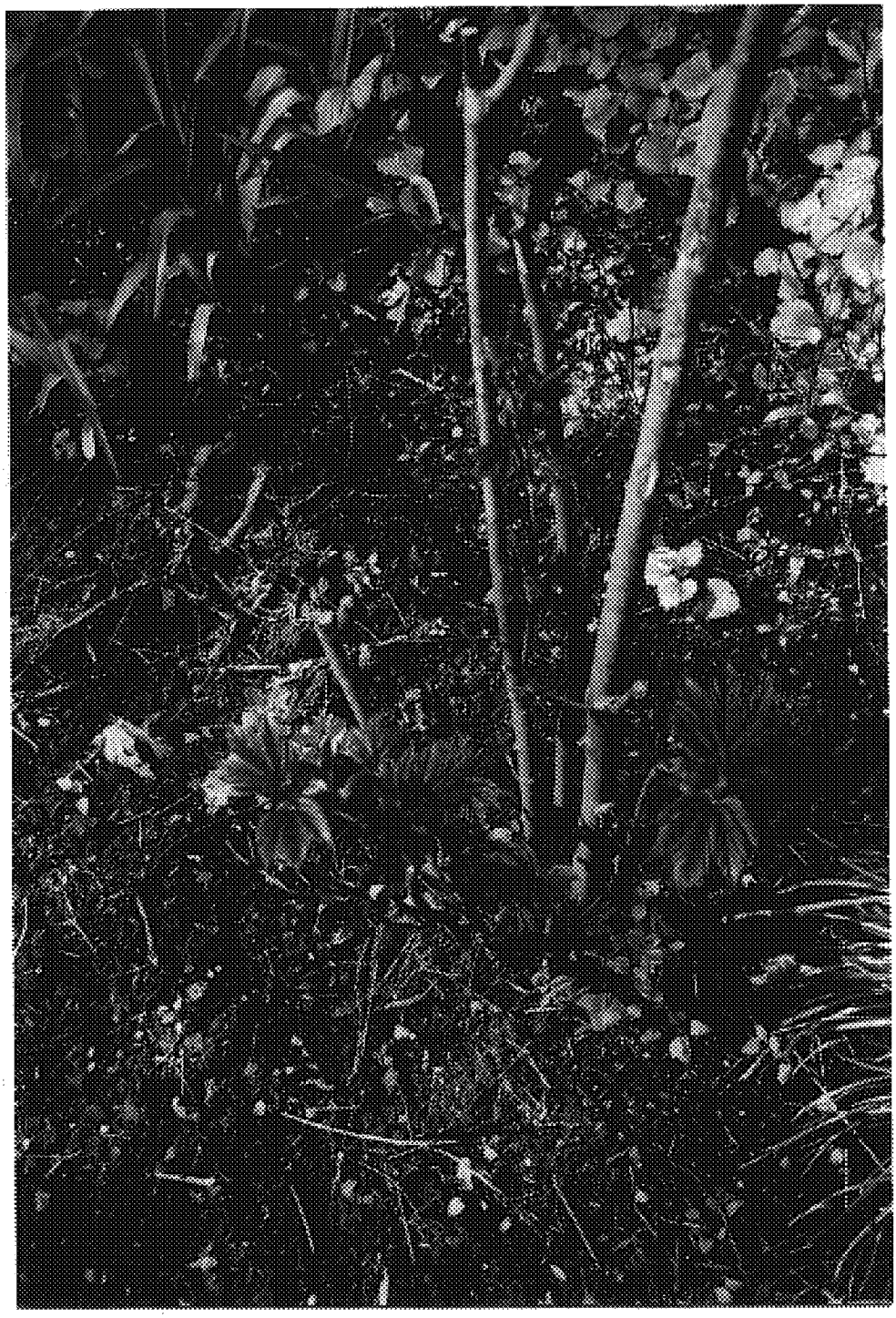

FIG. 5*a* is a photograph of 'Tunpetti' produced by chip budding in a hothouse, especially showing an upper leaf surface;

FIG. 5*b* is a photograph of 'Tunpetti' produced by chip budding in a hothouse, especially showing a lower leaf surface; and, FIG. 6 is a photograph showing the upper leaf surface during spring.

DETAILED DESCRIPTION

The following is a detailed description of the new *Acer pseudoplatanus* variety 'Tunpetti' with colour terminology in accordance with The Royal Horticultural Society Colour Chart 2001 (R.H.S.), published by The Royal Horticultural Society of London. The observations are of trees growing in London, Ontario, Canada.

Growth habit: Upright, well-branched medium vigour. Observed annual terminal branch growth is in the range of 40–70 cm, and annual lateral branch growth is in the range of 20–30 cm.

Size: It is predicted that a fully mature tree will assume a height of approximately 40–60 feet, with a wide-spreading-crown of about 20–30 feet, which is typical of the species *Acer pseudoplatanus.*

Bark: Smooth except for vertical fissuring and very slight scaliness.

Immature bark colour: Grey-brown R.H.S. N199A.

Mature bark colour: Grey-green R.H.S. 195A.

Branches: Current season branches are 90–130 cm in length. The observed average branch diameter is about 12 mm.

Branch internode length: Approximately 10–20 cm.

Leaves: Opposite, simple, and palmately lobed. Leaves moderately cut into three to five lobes.

Blade size: Approximately 15–18 cm in length and approximately 15–20 cm in width.

Base: Cordate.

Apex: Acuminate.

Margin: Coarsely serrate.

Pubescence: Upper surface glabrous, underside of the leaf has general weak pubescence which is stronger along the veins.

Surface: Slightly rugose.

Leaf colour: During the spring, the upper surface is copper coloured, R.H.S. 178A to R.H.S. 178C, with the lower surface leaf colouration being R.H.S. 37A. During the summer, the upper surface is dark green near to R.H.S. 137A, and the underside is more grey than R.H.S. N186C. During the fall, the foliage turns a brilliant yellow, upper leaf surface R.H.S. 14B, and the underside is R.H.S. 48A to R.H.S. 48B.

Leaf veins: Palmately veined, veins on upper surface R.H.S. 145B, underside veins R.H.S. 144B, secondary veins are paler than N186C.

Petiole: Glabrous. Size: Approximately 16–19 cm in length. The average petiole diameter is 3 mm. Colour: Upper surface R.H.S. 46A to R.H.S. 46B, and underside R.H.S. 144B.

Bud: Conical, narrow acute. Color R.H.S. 12B. The average bud size is 10 mm.

Flowers: No flowers have been observed on 4 year-old plants.

Disease resistance: Exceptional resistance to *Rhytisma acerinum,* also known as "tar spot", with no occurrence observed during 4 years of propagation.

Hardiness; heat/cold resistance: The plant has been successfully tested in the following zones: Zone 6 (London, Ontario, Canada); Zone 5 (Ottawa, Ontario, Canada and Kingston, Ontario, Canada) and Zone 4 (Sudbury, Ontario, Canada).

What is claimed:

1. A new and distinct variety of sycamore maple tree named "Tunpetti" substantially as herein shown and described.

* * * * *